US012805831B1

(12) United States Patent
Newell

(10) Patent No.: US 12,805,831 B1
(45) Date of Patent: Nov. 24, 2026

(54) SYSTEM AND METHOD FOR CONTINUOUSLY RECORDING INTRACRANIAL B WAVES USING DOPPLER ULTRASOUND TO TRACK AND ENHANCE THE SLEEP SURGE IN GLYMPHATIC FLOW TO PREVENT COGNITIVE DECLINE AND ALZHEIMER'S DISEASE

(71) Applicant: David W. Newell, Seattle, WA (US)

(72) Inventor: David W. Newell, Seattle, WA (US)

( * ) Notice: Subject to any disclaimer, the term of this patent is extended or adjusted under 35 U.S.C. 154(b) by 0 days.

(21) Appl. No.: 19/548,798

(22) Filed: Feb. 24, 2026

Related U.S. Application Data

(63) Continuation of application No. PCT/US2025/048701, filed on Sep. 30, 2025.

(60) Provisional application No. 63/701,527, filed on Sep. 30, 2024.

(51) Int. Cl.
*A61B 8/08* (2006.01)
*A61B 8/00* (2006.01)

(52) U.S. Cl.
CPC .......... *A61B 8/0816* (2013.01); *A61B 8/4236* (2013.01); *A61B 8/5207* (2013.01); *A61B 8/5269* (2013.01); *A61B 8/54* (2013.01)

(58) Field of Classification Search
CPC ... A61B 8/0816; A61B 8/4236; A61B 8/5207; A61B 8/5269; A61B 8/54
See application file for complete search history.

(56) References Cited

U.S. PATENT DOCUMENTS

| | | | | |
|---|---|---|---|---|
| 2019/0030374 | A1 | 1/2019 | Carpentier et al. | |
| 2019/0308036 | A1* | 10/2019 | Ebbini | A61B 8/4236 |
| 2020/0297211 | A1 | 9/2020 | Jordan | |
| 2020/0346028 | A1* | 11/2020 | Arendash | A61N 1/0456 |
| 2021/0060609 | A1 | 3/2021 | Rock | |
| 2022/0072128 | A1 | 3/2022 | Airan | |
| 2023/0210495 | A1* | 7/2023 | Lee | A61B 8/4236 600/459 |

FOREIGN PATENT DOCUMENTS

WO 2024167902 A1 8/2024

OTHER PUBLICATIONS

International Search Report and Written Opinion of the International Searching Authority mailed Dec. 12, 2025, issued in corresponding International Application No. PCT/US2025/048701, filed Sep. 30, 2025, 12 pages.
Newell, D.W., et al. Physiological Mechanisms and Significance of Intracranial B Waves. Frontiers in Neurology [online], May 16, 2022 (May 16, 2022) [retrieved on Nov. 20, 2025] Retrieved from the Internet: [URL: https://pubmed.ncbi.nlm.nih.gov/35651339/] [DOI:10.3389/fneur.2022.872701].
(Continued)

*Primary Examiner* — Amal Aly Farag
(74) *Attorney, Agent, or Firm* — CHRISTENSEN O'CONNOR JOHNSON KINDNESS PLLC

(57) ABSTRACT

A system for improving cerebrospinal fluid clearance through a glymphatic system, while a patient is sleeping, resting, or a combination of sleeping and resting. The method includes measuring ultrasound data with one or more ultrasound emitters and extracting B-wave oscillations from the ultrasound data.

15 Claims, 5 Drawing Sheets

(56) References Cited

OTHER PUBLICATIONS

Gumeler, E., et al. Assessment of glymphatic function in narcolepsy using DTI-ALPS index. Sleep Medicine 101 [online], Dec. 9, 2022 (Dec. 9, 2022) [retrieved on Nov. 20, 2025] Retrieved from the Internet: [URL: https://pubmed.ncbi.nlm.nih.gov/36535226/] [DOI: 10.1016/j.sleep.2022.12.002].

* cited by examiner

SYSTEM AND METHOD FOR CONTINUOUSLY RECORDING INTRACRANIAL B WAVES USING DOPPLER ULTRASOUND TO TRACK AND ENHANCE THE SLEEP SURGE IN GLYMPHATIC FLOW TO PREVENT COGNITIVE DECLINE AND ALZHEIMER'S DISEASE

CROSS-REFERENCE TO RELATED APPLICATIONS

This application is a U.S. Continuation of PCT/US2025/048701, filed Sep. 30, 2025, which claims the benefit of U.S. Provisional Application 63/701,527 filed Sep. 30, 2024, the entire disclosure of which is hereby incorporated by reference.

BACKGROUND

The glymphatic system is essential for clearing neurotoxic waste from the brain via cerebrospinal fluid (CSF) movement during sleep. This clearance process is tightly coupled with slow oscillatory intracranial hemodynamics, such as intracranial B waves: slow-frequency fluctuations in cerebral blood flow.

Decreased slow-wave sleep and glymphatic clearance have been implicated in the pathogenesis of Alzheimer's disease. Prior studies have demonstrated that CSF influx and clearance are amplified during non-REM sleep and correlate with large-scale neurovascular oscillations.

Further, there has been in vivo evidence of neurovascular coupling dynamics aligning with sleep-stage transitions. These studies outlined the role of arterial pulsation and glial channel integrity in CSF flow efficiency. However, there remains a lack of noninvasive systems for continuous monitoring and real-time enhancement of these clearance mechanisms.

Existing neurostimulation devices and sleep monitoring systems fail to integrate CSF flow dynamics, vascular signal detection, and glymphatic enhancement protocols.

Accordingly, devices, systems, and methods to record and enhance B waves using Doppler ultrasound and closed-loop neuromodulation are needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, disclosed herein is a system for detecting intracranial B waves, including an ultrasound emitter configured for administering ultrasound, and a smart device, wherein the smart device comprises a processor configured for receiving ultrasound data from the transcranial ultrasound patch, and extracting B-wave oscillations from the ultrasound data.

In some embodiments, the ultrasound emitter is a transcranial ultrasound patch. In some embodiments, switching a frequency of the ultrasound based on one or more signal quality metrics of the B-wave oscillations, wherein switching the frequency improves a visibility of the B-wave oscillations.

In some embodiments, switching a frequency of the ultrasound comprises switching from a first transducer configured for emitting a first ultrasound at a first frequency to a second transducer configured for emitting a second ultrasound at a second frequency. In some embodiments, all transducers of one or more transducers switch from a first frequency to a second frequency.

In some embodiments, the frequency of the ultrasound energy is switched between 2 MHz and 1 MHz. In some embodiments, switching from 2 MHz to 1 MHz increases intracranial penetration for B-wave detection in patients with increased skull thickness or calcification. In some embodiments, the one or more signal quality metrics are a reduction in signal penetration, a reflection, or an amplitude detected at an initial operating frequency of the ultrasound data. In some embodiments, the one or more signal quality metrics is a detection of a drop below a signal-to-noise ratio (SNR) threshold. In some embodiments, the switching occurs in real time without manual intervention. In some embodiments, the ultrasound emitter comprises one or more transducers. In some embodiments, the one or more transducers comprise capacitive micromachined ultrasonic transducers (CMUTs), piezoelectric microlaminated elements, or a combination thereof. In some embodiments, frequency switching is reversed from 1 MHz back to 2 MHz when the one or more signal quality metrics meet an operational threshold.

In some embodiments, the smart device is further configured for storing a frequency switching protocol based on the frequency switching. In some embodiments, the smart device is further configured to generate a glymphatic index output derived from an amplitude and a frequency of the B-wave oscillations. In some embodiments, the smart device is further configured to display the glymphatic index output before and after administering neuromodulation or intervention.

In another aspect, disclosed herein is a method for improving cerebrospinal fluid clearance through a glymphatic system, while a patient is sleeping, resting, or a combination thereof, the method including measuring ultrasound data, extracting B-wave oscillations from the ultrasound data, selecting a target region of a brain for neural modulation, and administering neural modulation to the target region, wherein the neural modulation is configured for increasing one or more B-wave parameters.

In some embodiments, the neural modulation comprises administering a drug before the patient falls asleep. In some embodiments, the neural modulation is administering a drug while the patient is asleep.

In some embodiments, the neuromodulation is a plurality of pulses emitted from one or more transducers. In some embodiments, the plurality of pulses has a frequency of between about 400 Hz and about 1 MHz. In some embodiments, the plurality of pulses has a duration of between about 1 microsecond and about 1 minute.

In some embodiments, the neural modulation includes emitting an acoustic stimulus. In some embodiments, the acoustic stimulus comprises a broadband noise signal. In some embodiments, the acoustic stimulus is selected from pink noise, white noise, or filtered noise. In some embodiments, the acoustic stimulus has a frequency of about 1 Hz to about 20 kHz. In some embodiments, the acoustic stimulus comprises pulsed bursts of pink noise synchronized to intracranial B-waves or EEG slow waves. In some embodiments, the acoustic stimulus comprises amplitude- or frequency-modulated sound is configured for enhancing slow-wave oscillations or vascular B-waves. In some embodiments, the acoustic stimulus is delivered at a sampling rate sufficient to reproduce frequencies up to about 20 KHz.

In some embodiments, the neural modulation includes delivering transcranial direct current (DC), transcranial alternating current (AC) stimulation, or a combination thereof. In some embodiments, the neural modulation includes delivering transcranial magnetic stimulation (TMS). In some embodiments, the neural modulation includes delivering transcranial pressure.

In yet another aspect, disclosed herein is a transcranial ultrasound patch system for improving cerebrospinal fluid clearance through perivascular pathways, comprising a transcranial ultrasound patch, a smart device, wherein the smart device comprises a processor configured for receiving ultrasound data from the transcranial ultrasound patch, extracting B-wave oscillations from the ultrasound data, selecting a target region for neural modulation, and administering neural modulation to the target region, wherein the neural modulation is configured for increasing one or more B-wave parameters.

In some embodiments, the one or more B-wave parameters comprise an amplitude, a frequency, or a combination thereof.

In some embodiments, the transcranial ultrasound patch includes a first electrode, a second electrode, one or more transducers disposed between the first electrode and the second electrode, and a shielding layer.

In some embodiments, the one or more transducers is a transducer array. In some embodiments, the transducer array is an 8 by 8 transducer array. In some embodiments, the neuromodulation is a plurality of pulses emitted from the one or more transducers. In some embodiments, the plurality of pulses has a frequency of between about 400 Hz and about 1 MHz. In some embodiments, the plurality of pulses has a duration of between about 1 microsecond and about 1 minute.

In some embodiments, the patch further includes one or more leads configured for measuring an electroencephalogram (EEG) of the user. In some embodiments, the patch further includes an inertial sensor configured for measuring the location of the patch. In some embodiments, the patch further includes a temperature sensor configured for measuring a temperature of a user's head. In some embodiments, the patch further includes a charging unit configured to supply power to the patch.

In some embodiments, the system further includes a neural modulation module. In some embodiments, the neural stimulation module is a micro-speaker configured for emitting an acoustic stimulus. In some embodiments, the acoustic stimulus comprises a broadband noise signal. In some embodiments, the acoustic stimulus is selected from pink noise, white noise, or filtered noise. In some embodiments, the acoustic stimulus has a frequency of about 1 Hz to about 20 kHz.

In some embodiments, the acoustic stimulus comprises pulsed bursts of pink noise synchronized to intracranial B-waves or EEG slow waves. In some embodiments, the acoustic stimulus comprises amplitude- or frequency-modulated sound is configured for enhancing slow-wave oscillations or vascular B-waves. In some embodiments, the acoustic stimulus is delivered at a sampling rate sufficient to reproduce frequencies up to about 20 kHz.

In some embodiments, the neural stimulation module is a current-controlled stimulator configured for delivering transcranial direct current (DC) and transcranial alternating current (AC) stimulation.

In some embodiments, the patch further includes an adhesive configured to secure the patch to a user's head. In some embodiments, the system further includes a headband coupled to the patch configured for securing the patch to a user's head.

In yet another aspect, disclosed herein is a method of preventing Alzheimer's with the system disclosed herein, the method including measuring ultrasound data, extracting B-wave oscillations from the ultrasound data, selecting a target region of a brain for neural modulation, and administering neural modulation to the target region, where the neural modulation is configured for increasing one or more B-wave parameters.

In another aspect, disclosed herein is a method of treating a traumatic brain injury with the system disclosed herein, the method including measuring ultrasound data, extracting B-wave oscillations from the ultrasound data, selecting a target region of a brain for neural modulation, and administering neural modulation to the target region, wherein the neural modulation is configured for increasing one or more B-wave parameters.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figures 1A, 1B, 1C, 1D, 1E, 1F:
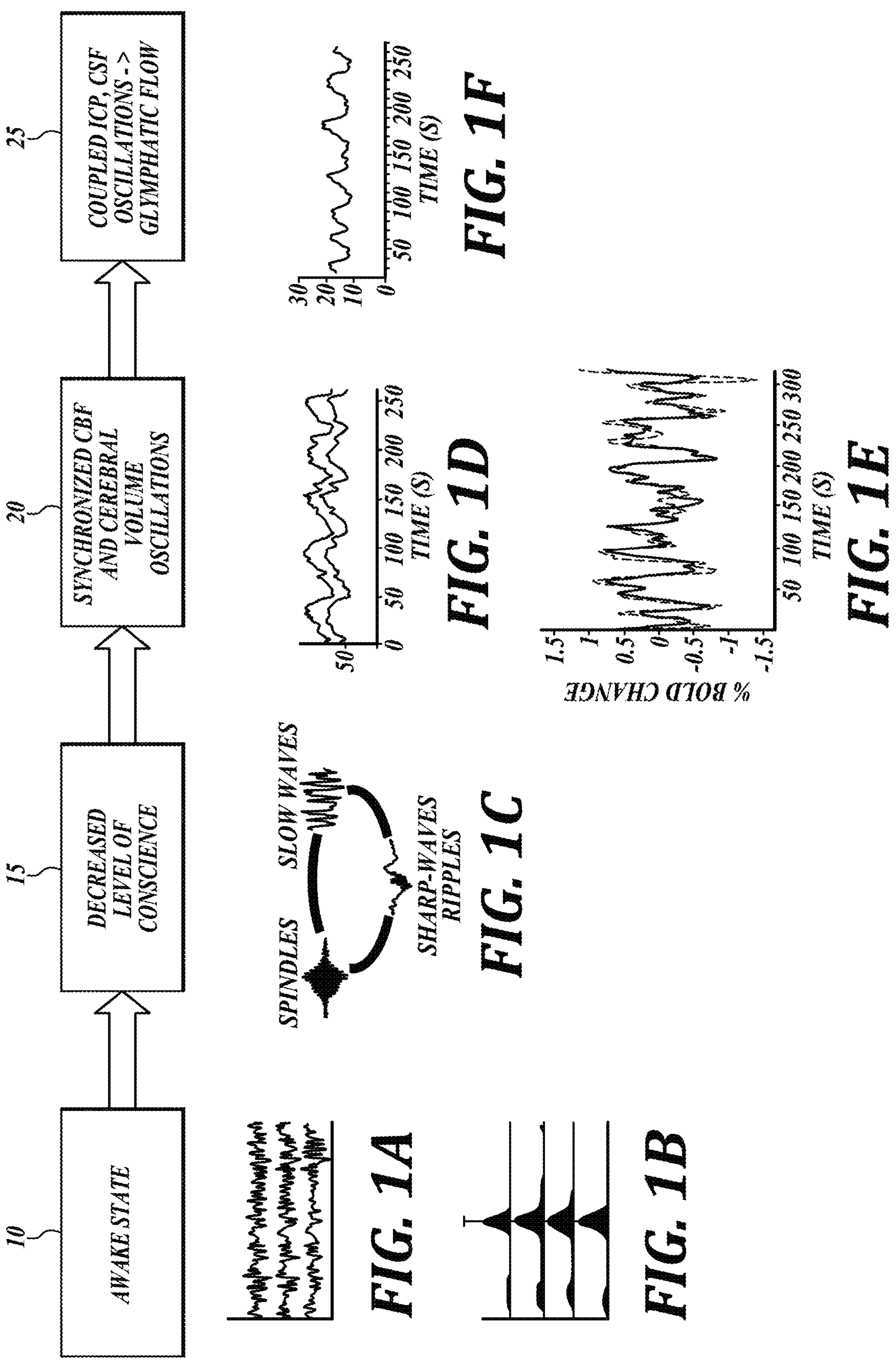
FIGS. 1A-1F show a process diagram of sleeping stages and intracranial B-waves, in accordance with the present technology.

Discloed herein are wearable, transcranial Doppler ultrasound using a probe or patch to continuously record intracranial B waves, analyze slow cerebral blood flow oscillations, and wirelessly transmit data to an external device.

The system optionally administers pharmacologic or supplemental interventions and provides closed-loop neuromodulation triggered by EEG slow-wave detection to amplify B waves and improve glymphatic clearance.

In some embodiments, the system disclosed herein includes B wave detection via transcranial Doppler ultrasound, EEG-based detection of slow-wave sleep, drug or supplement-assisted glymphatic modulation, and closed-loop neurostimulation to boost slow waves and CSF oscillations.

In some embodiments, transcranial Doppler patch measures slow blood flow velocity oscillations through the temporal bone using 2-4 MHz frequency ultrasound. Oscillations with a periodicity of 0.3-4.0 cpm are captured as indicators of B waves. In some embodiments, The EEG module concurrently records brain activity to identify onset and phases of slow-wave sleep, and EEG slow oscillations (0.3-4.0 cpm) (delta band: 0.5-4 Hz).

In some embodiments, pharmacologic or supplemental agents known to enhance glymphatic flow (e.g., alpha-2 agonists like tizanidine, dexmedetomidine, or natural compounds like resveratrol, to enhance neurovascular coupling) are optionally administered prior to or during sleep.

In some embodiments, a feedback loop modulates neurostimulation (e.g., transcranial direct current stimulation or ultrasound bursts) based on real-time EEG and B wave metrics. Neuromodulation is delivered to reinforce and phase-lock cerebral slow waves.

In some embodiments, wireless communication (e.g., Bluetooth, wifi, Low Energy) allows real-time data transmission to a bedside or mobile device. The system can visualize oscillation amplitude, frequency, and trends to guide dosing, neuromodulation, or sleep optimization. The data may be encrypted, timestamped, and/or stored locally or in the cloud for long-term tracking of sleep-related clearance metrics.

FIGS. 1A-1F show a process diagram of sleeping stages and intracranial B-waves, in accordance with the present technology. Four main sleep stages are shown: awake state 10, decreased level of consciousness 15, synchronized cerebral blood flow (CBF) and cerebral blood volume oscillations 20, and coupled intracranial pressure (ICP) and cerebrospinal fluid (CSF) oscillations, leading to glymphatic flow 25.

In the awake state 10, CBF may fluctuate based on tasks, brain activities, and/or hemodynamics. Shown in awake state 10 is raw EEG (FIG. 1A), and Fourier analysis of a predominant alpha rhythm (8-12 Hz) (FIG. 1B) as is typical in awake state 10. Brain fluctuations in the awake state 10 are normal, including gamma rhythms between about 32-100 Hz, beta rhythms between about 13-32 Hz, alpha rhythms between about 8-13 Hz, theta rhythms between about 4-8 Hz, and delta rhythms between about 0.5-4 Hz.

In a decreased level of consciousness 15, there is a predominant delta wave EEG of about 0-4 Hz. A person may transition from the awake state 10 to a decreased level of consciousness 15 through deep resting and non-REM sleep, sedation, anesthesia, and/or a brain injury or coma. In the decreased level of consciousness 15, there are repeating episodes of faster EEG activity, which occurs between 0.3 to 4 times per minute. This EEG activity may include spindles, slow waves, and sharp-waves ripples (FIG. 1C). Spectral edge tracing of EEG fluctuations transition from delta rhythms to faster theta frequencies and synchronize with B-waves. It is believed this process originates and is modulated by the locus coeruleus of the brain.

Eventually, the CBF and cerebral blood volume oscillations synchronize, in state 20. Transcranial Doppler recordings of middle cerebral artery (MCA) velocity profiles in this state show B waves of MCA velocity, reflecting CBF oscillations (FIG. 1D). The MCA velocity and CBF oscillations may range from 0.3-4 cycles per minute at about 0.005 to about 0.067 Hz Both periodic EEG fluctuations and neurovascular coupling may lead to state 20. In state 20, MRI bold signal tracing can detect CBF oscillations at the same frequency (FIG. 1E).

In state 25, the coupled ICP and CSP oscillations lead to glymphatic flow. In this state 25, intracranial pressure B-waves may be visible (FIG. 1F). MRI CSF flow imaging of the 4th ventricle shows inflow of new CSF in state 25.

Figure 2B:
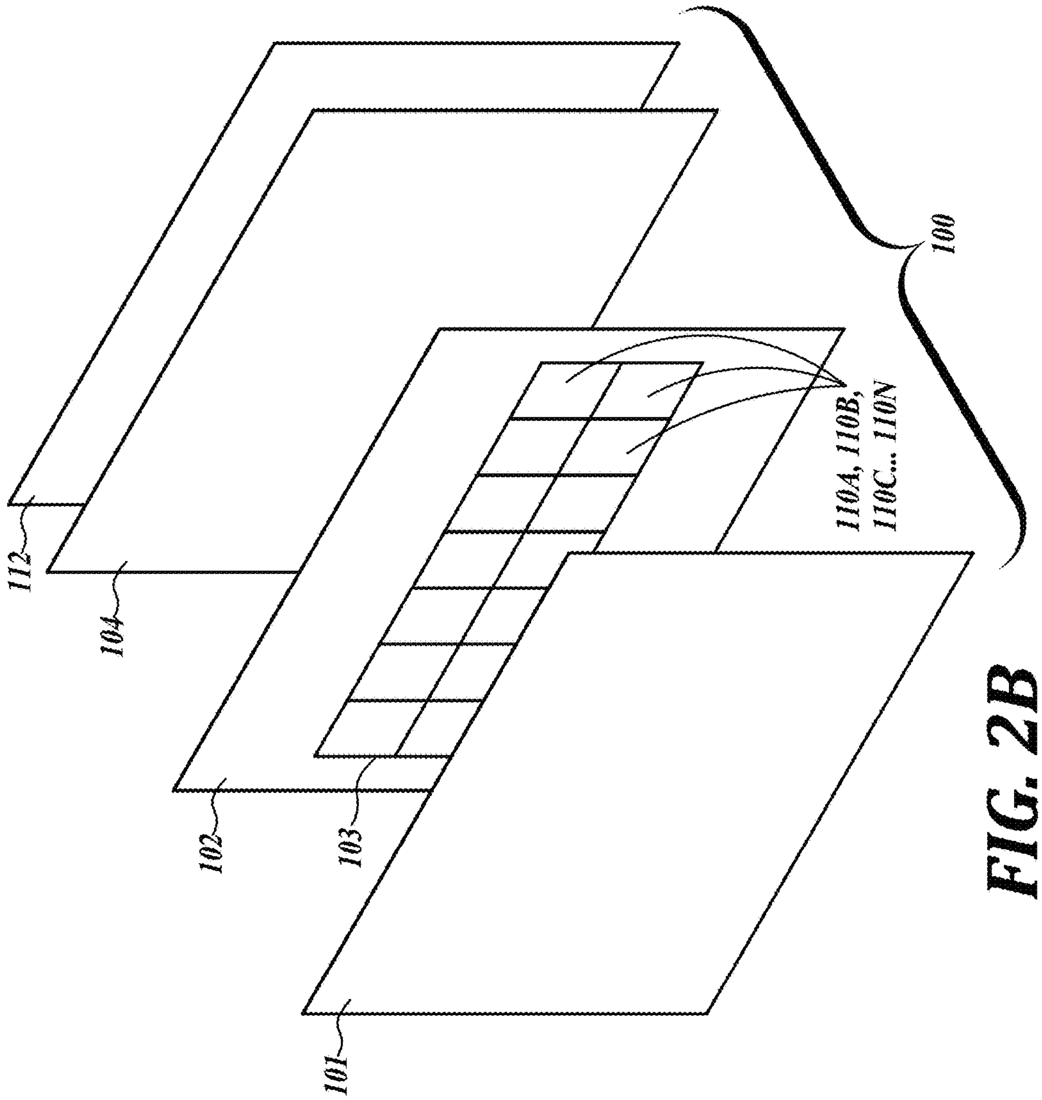
FIGS. 2A-2C are example transcranial ultrasound patches, in accordance with the present technology.
Figure 2A:
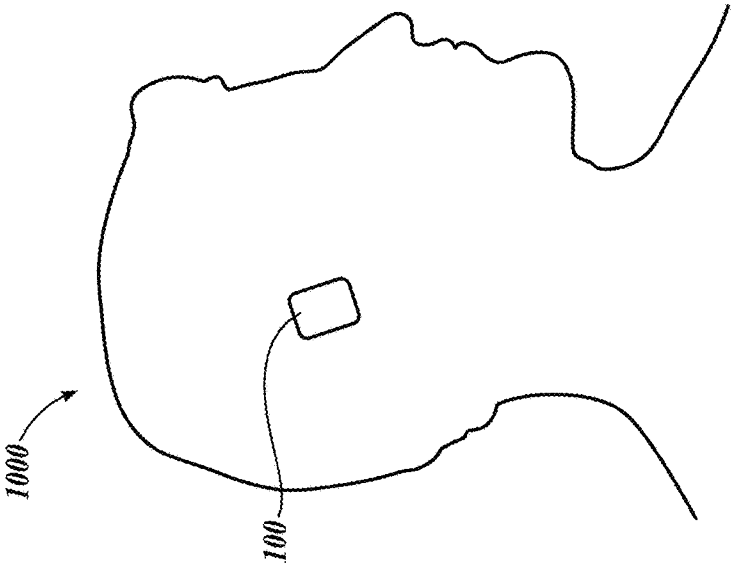
Figure 2C:
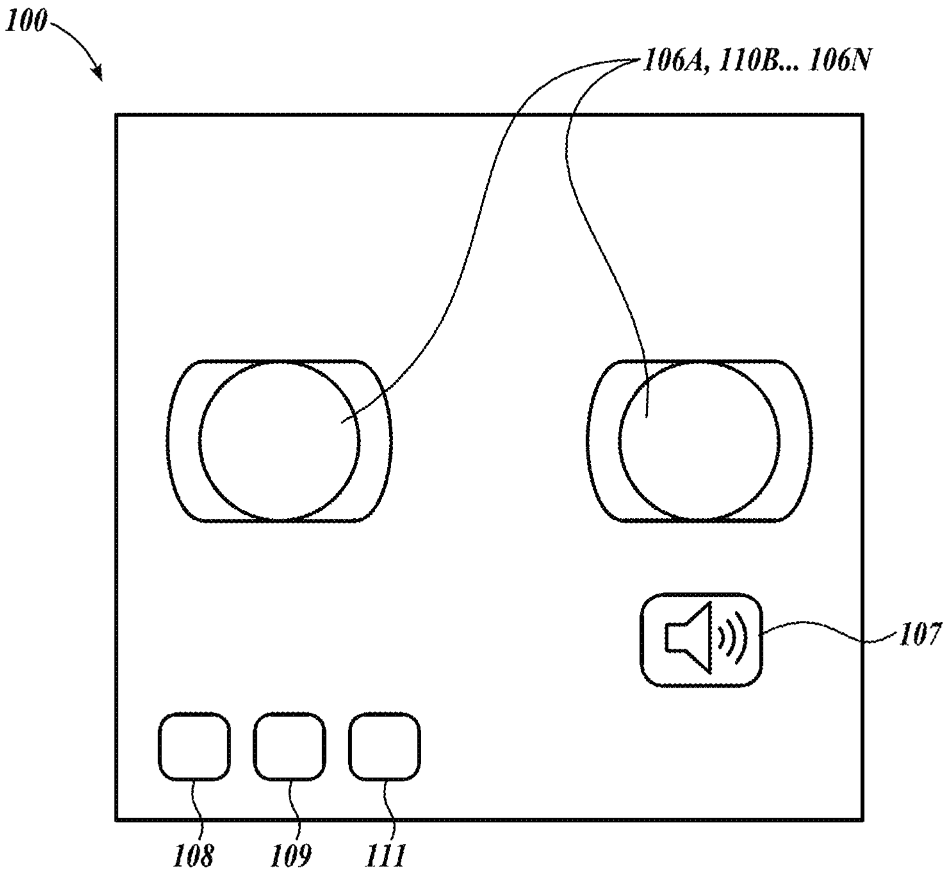

FIGS. 2A-2C are example transcranial ultrasound patches 100, in accordance with the present technology.

Figure 3:
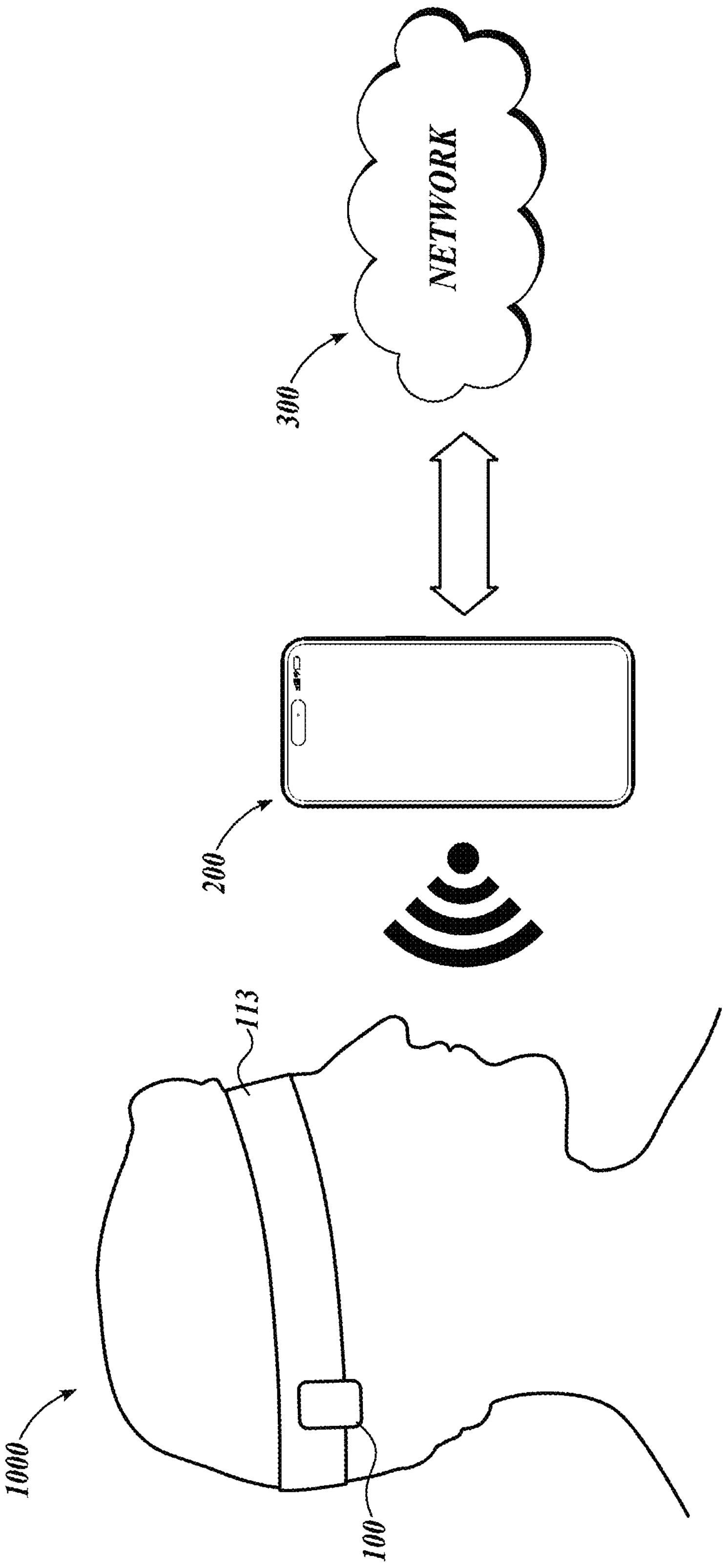
FIG. 3 is an example transcranial ultrasound patch system, in accordance with the present technology.

FIG. 2A shows a transcranial ultrasound patch 100 attached to a user (or patient) 1000. In some embodiments, the transcranial ultrasound patch 100 includes an adhesive (such as adhesive 112) or attachment (such as headband 113) configured to removably couple the transcranial ultrasound patch 100 to the user 1000. In operation, the transcranial ultrasound patch is configured to measure ultrasound data of the user 1000. In some embodiments, the ultrasound patch 100 is communicatively coupled to an external device (as shown in FIG. 3). The ultrasound patch 100 may transmit ultrasound data to the external device for additional processing.

In some embodiments, the methods and systems described herein are performed with an ultrasound emitter (such as transcranial ultrasound patch 100). In some embodiments, the ultrasound emitter is an ultrasound probe. In some embodiments, the ultrasound emitter is a transcranial ultrasound probe. In some embodiments, the ultrasound emitter comprises one or more transducers (such as shown in FIG. 2B).

In one aspect, disclosed herein is a system for monitoring the brain of a patient, including a transcranial ultrasound patch comprising one or more transducers configured for administering ultrasound, and a smart device, where the smart device comprises a processor configured for receiving ultrasound data from the transcranial ultrasound patch, and switching a frequency of the ultrasound energy based on one or more signal quality metrics of the ultrasound data. In some embodiments, this system may be able to monitor and detect B-waves, but it may also be for the purpose of monitoring brain metrics such as ultrasound, brain waves, or other brain metrics.

FIG. 2B is an exploded view of the transcranial ultrasound patch 100 of FIG. 2A. In some embodiments, the transcranial ultrasound patch 100 includes a plurality of layers. In some embodiments, the plurality of layers includes: a first electrode 101, a second electrode 102, one or more transducers 103, and a shielding layer 104. In some embodiments, the one or more transducers 103 is disposed between the first electrode 101 and the second electrode 102.

In some embodiments, the first electrode 101 is a common ground electrode. In some embodiments, the second electrode 102 includes one or more layers. In some embodiments, the second electrode 102 is a five-layer electrode. In some embodiments, the second electrode 102 is a stretchable electrode.

In some embodiments, the one or more transducers 103 are one or more piezoelectric transducers. In some embodiments, the one or more transducers 103 is a transducer array, made up of a plurality of transducers 110A, 110B, 110C . . . 110N. In some embodiments, the transducer array is an 8 by 8 transducer array. In some embodiments, the one or more transducers 103 are capacitive micromachined ultrasonic transducers (CMUTs), piezoelectric microlaminated elements, or a combination thereof.

In some embodiments, each transducer of the one or more transducers may emit a single frequency. For example, in some embodiments, a first transducer of the one or more transducer is configured to emit a first ultrasound at a first frequency and a second transducer of the one or more transducers is configured to emit a second ultrasound at a second frequency. Accordingly, "frequency switching" as used herein may refer to emitting the first ultrasound at the first frequency with the first transducer and then switching to emitting a second ultrasound at the second frequency with the second transducer.

In other embodiments the one or more transducers may be configured to deliver ultrasound at a plurality of frequencies. For example, in some embodiments, the ultrasound emitter may include only a single transducer configured to emit ultrasound at two frequencies. In some embodiments, the one or more transducers may be a tunable dual-frequency transducer configured to emit ultrasound at two different frequencies through electrode configuration or material polarization changes in piezoelectric micromachined ultrasonic transducers (PMUTs). This capability allows for enhanced imaging and sensing by enabling, for instance, the combination of high-resolution imaging for superficial structures and deep penetration for deeper ones within a single device. Tunable frequencies are achieved by altering the transducer's geometry, electrode arrangement, or by applying a DC bias voltage to change the polarization of the piezoelectric material, which adjusts the vibration modes and therefore the emitted frequencies. Accordingly, "frequency switching" as used herein may refer to switching from a first frequency to a second frequency with a same or all transducers of the one or more transducers.

In operation, the one or more transducers 103 may administer neuromodulation to a user (such as user 1000). In some embodiments, the neuromodulation is a plurality of pulses emitted from the one or more transducers 103. In some embodiments, the plurality of pulses has a frequency of between about 400 Hz and about 1 MHz. In some embodiments, the plurality of pulses has a duration of between about 1 microsecond and about 1 minute.

In some embodiments, the shielding layer 104 is a copper mesh shielding layer. In some embodiments, the shielding layer is an electromagnetic shielding layer.

In some embodiments, the transcranial ultrasound patch 100 is encapsulated by an elastomer. In some embodiments, the transcranial ultrasound patch 100 may include an attachment or adhesive 112 for coupling the transcranial ultrasound patch 100 to a user (such as user 1000).

FIG. 2C is an external view of a transcranial ultrasound patch 100. In some embodiments, the transcranial ultrasound patch further includes one or more leads 106A, 106C . . . 106N, an inertial sensor 108, a temperature sensor 109, and a charging unit 111.

In some embodiments, the one or more leads 106A, 160B . . . 106N are configured for measuring an electroencephalogram (EEG) of the user. In some embodiments, the one or more leads 106A, 160B . . . 106N are configured to contact a user (such as user 1000) to measure the EEG. The transcranial ultrasound patch 100 may transmit the measured EEG to an external device as shown in FIG. 3.

In some embodiments, the inertial sensor 108 is configured for measuring the location of the patch. In some embodiments, the temperature sensor 109 is configured for measuring a temperature of a user's head. In some embodiments, the charging unit 111 is configured to supply power to the patch 100.

In some embodiments, the transcranial ultrasound patch 100 further includes a neural modulation module 107.

In some embodiments, the neural stimulation module 107 is a micro-speaker configured for emitting an acoustic stimulus. In some embodiments, the acoustic stimulus comprises a broadband noise signal. In some embodiments, the acoustic stimulus is selected from pink noise, white noise, or filtered noise. In some embodiments, the acoustic stimulus has a frequency of about 1 Hz to about 20 kHz. In some embodiments, acoustic stimulus comprises pulsed bursts of pink noise synchronized to intracranial B-waves or EEG slow waves. In some embodiments, acoustic stimulus comprises amplitude- or frequency-modulated sound is configured for enhancing slow-wave oscillations or vascular B-waves. In some embodiments, the acoustic stimulus is delivered at a sampling rate sufficient to reproduce frequencies up to about 20 kHz.

In some embodiments, the neural stimulation module 107 is a current-controlled stimulator configured for delivering transcranial direct current (DC) and transcranial alternating current (AC) stimulation.

FIG. 3 is an example transcranial ultrasound patch system 2000, in accordance with the present technology. In some embodiments, the transcranial ultrasound patch system 2000 includes a transcranial ultrasound patch 200 as shown and described herein. In some embodiments, the transcranial ultrasound patch 200 includes a headband 113 configured to hold the patch 200 in contact with the user 1000. The system 2000 may further include an external device (or "smart device") 200. In some embodiments, the smart device 200 is communicatively coupled to a network 300.

In some embodiments, the smart device 200 includes a processor configured for receiving ultrasound data from the transcranial ultrasound patch 100, extracting B-wave oscillations from the ultrasound data, selecting a target region for neural modulation, and administering neural modulation to the target region, where the neural modulation is configured for increasing one or more B-wave parameters. In some embodiments, the one or more B-wave parameters include an amplitude, a frequency, or a combination thereof. In some embodiments, the neural modulation is administered by the transcranial ultrasound patch 100 (such as with neural stimulation module 107).

In some embodiments, the smart device is configured to adjust (or "switch") a frequency of the ultrasound administered by the transcranial ultrasound patch 100 in real time to improve a readability, visibility, or quality of the B-wave oscillations. In some embodiments, the smart device 200 is configured to switch the frequency of the ultrasound from 2 MHz to 1 MHz. In some embodiments, the smart device 200 is configured to switch the frequency of the ultrasound from about 1.5 to about 3 MHz to about 0.1 to about 1.4 MHz. In some embodiments, the smart device 200 is configured for switching a frequency of the ultrasound energy based on one or more signal quality metrics of the B-wave oscillations, wherein switching the frequency improves a visibility of the B-wave oscillations.

In some embodiments, the frequency of the ultrasound is switched between 2 MHz and 1 MHz. In some embodiments, the frequency of the ultrasound is switched from about 1.5 to about 3 MHz and 0.1 to about 1.4 MHz. In some embodiments, switching from about 1.5 to about 3 MHz to about 0.1 to about 1.4 MHZ, increases intracranial penetration for B-wave detection in patients with increased skull thickness or calcification. In some embodiments, the one or more signal quality metrics are a reduction in signal penetration, a reflection, or an amplitude detected at an initial operating frequency of the ultrasound data. In some embodiments, the one or more signal quality metrics is a detection of a drop below a signal-to-noise ratio (SNR) threshold. In some embodiments, the switching occurs in real time without manual intervention. In this manner, the smart device 200 may monitor the B-wave oscillations as the B-wave oscillations are measured and then adjust the quality of the B-wave oscillations in real time by switching the frequency of the ultrasound.

In some embodiments, the one or more transducers (such as one or more transducers 103) comprise capacitive micromachined ultrasonic transducers (CMUTs), piezoelectric microlaminated elements, or a combination thereof.

In some embodiments, frequency switching is reversed from about 0.1 to about 1.4 MHz and about 1.5 to about 3 MHz. In some embodiments, frequency switching is reversed from about 1 MHz back to 2 MHz when the one or more signal quality metrics meet an operational threshold.

In some embodiments, the smart device 200 is further configured for storing a frequency switching protocol based on the frequency switching. In some embodiments, the smart device 200 is further configured to generate a glymphatic index output derived from an amplitude and a frequency of the B-wave oscillations. In some embodiments, the smart device 200 is further configured to display the glymphatic index output before and after administering neuromodulation or intervention.

Figure 4:
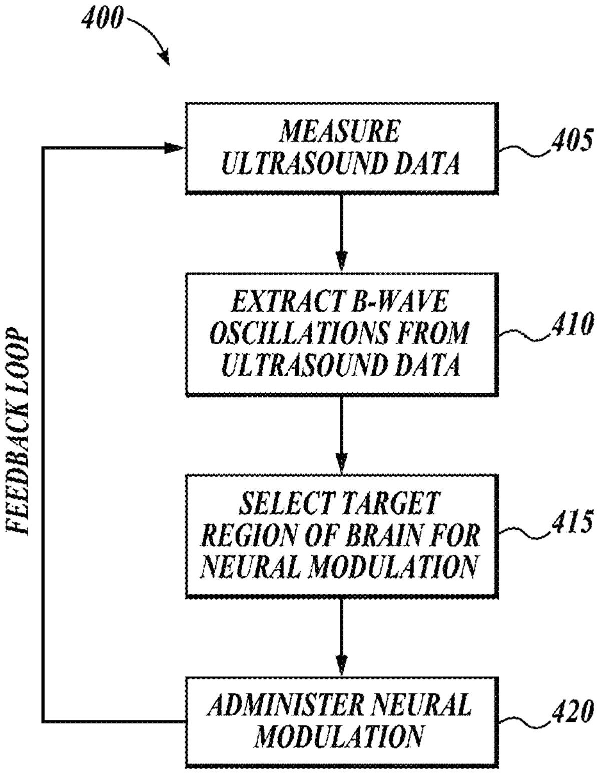
FIG. 4 is an example method of using the transcranial ultrasound patch system, in accordance with the present technology.

FIG. 4 is an example method 400 of using the transcranial ultrasound patch system, in accordance with the present technology. In some embodiments, method 400 may be carried out with a transcranial ultrasound patch (such as transcranial ultrasound patch 100). In some embodiments, the transcranial ultrasound patch may include one or more transducers (such as one or more transducers 103) and a neural stimulation module (such as neural stimulation module 107). In some embodiments, the transcranial ultrasound patch may be a part of a transcranial ultrasound patch system (such as system 2000), including a smart device (such as smart device 200).

In block 405, ultrasound data is measured. While the ultrasound data may be measured with any ultrasound emitting device, in some embodiments, the ultrasound data is measured with the transcranial ultrasound patch. In some embodiments, the one or more transducers of the transcranial ultrasound patch deliver ultrasound to a user (such as user 1000) to measure the ultrasound data.

In block 410, B-wave oscillations are extracted from the ultrasound data. In some embodiments, this step is performed by the smart device. In some embodiments, the B-wave oscillations are extracted with signal processing located on the smart device. In some embodiments, the ultrasound data may be further processed to calculate B-wave phase, Rsx index, intensity, and/or spectral power of the B-wave oscillations/ultrasound data. In some embodiments, the Rsx index is used as a control variable.

In block 415, a target region of the brain is selected for neural modulation. In some embodiments, the target region of the brain is selected from a cingulate gyrus, an amygdala, a thalamus, a hippocampus, or a combination thereof. In some embodiments, the target region may be selected by a user. In some embodiments, the target region may be selected by a healthcare provider, such as the user's doctor, registered nurse, specialist, or the like.

In block 420, neural modulation is administered. The neural modulation may be administered through a variety of sources including the smart device, the transcranial ultrasound device, or an external medical device. Further, the neural modulation may be administered in a variety of forms.

For example, in some embodiments, the neural modulation includes administering a drug before the patient (user) falls asleep or while the patient is asleep. In some embodiments, the drug is selected from alpha-2 agonists like tizanidine, dexmedetomidine, or natural compounds like resveratrol, to enhance neurovascular coupling.

In some embodiments, the neuromodulation is a plurality of pulses emitted from one or more transducers. In some embodiments, the plurality of pulses has a frequency of between about 400 Hz and about 1 MHz. In some embodiments, the plurality of pulses has a duration of between about 1 microsecond and about 1 minute.

In some embodiments, the neural modulation comprises emitting an acoustic stimulus. The acoustic stimulus may be emitted by the transcranial ultrasound patch (such as micro speaker neural stimulation module 107), the smart device, or an external speaker. In some embodiments, the acoustic stimulus comprises a broadband noise signal. In some embodiments, the acoustic stimulus is selected from pink noise, white noise, or filtered noise. In dome embodiments, the acoustic stimulus has a frequency of about 1 Hz to about 20 kHz. In some embodiments, the acoustic stimulus comprises pulsed bursts of pink noise synchronized to intracranial B-waves or EEG slow waves. Pink noise has been shown to enhance slow-wave sleep and related neurovascular oscillations. In some embodiments, the acoustic stimulus comprises amplitude- or frequency-modulated sound is configured for enhancing slow-wave oscillations or vascular B-waves. In some embodiments, acoustic stimulus is delivered at a sampling rate sufficient to reproduce frequencies up to about 20 kHz.

In some embodiments, the neural modulation includes delivering transcranial direct current (DC), transcranial alternating current (AC) stimulation, or a combination thereof.

In yet other embodiments, the neural modulation comprises delivering transcranial magnetic stimulation (TMS). In some embodiments, the neural modulation comprises delivering transcranial pressure.

One skilled in the art should recognize that some or all of the disclosed neural modulation may be administered separately, concurrently, in combination with, or simultaneously.

In some embodiments, the method 400 may include a feedback loop, where after neural modulation is administered, method 400 returns to block 405. In such embodiments, an AI classifier trained on B wave morphology may allow for automatic feedback gating. Monitoring of the effect on a user's B-waves in real time is thus enabled with method 400. In cases where a physician or medical provider is administering the neural modulation, (such as when the patient/user is asleep) the physician may adjust, modulate, stop, or start the neural modulation in response to the monitored B-waves.

It should be understood that method 400 should be interpreted as merely representative. In some embodiments, process blocks of method 400 may be performed simultaneously, sequentially, in a different order, or even omitted, without departing from the scope of this disclosure.

The present application may reference quantities and numbers. Unless specifically stated, such quantities and numbers are not to be considered restrictive, but representative of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the invention.

What is claimed is:

1. A system for detecting intracranial B waves, comprising:

an ultrasound emitter configured for administering ultrasound; and a smart device, wherein the smart device comprises a processor configured for:

receiving ultrasound data from the ultrasound emitter;

extracting B-wave oscillations from the ultrasound data;

switching a frequency of the ultrasound based on one or more signal quality metrics of the B-wave oscillations; and storing a frequency switching protocol based on the frequency switching.

2. The system of claim 1, wherein the ultrasound emitter is a transcranial ultrasound patch.

3. The system of claim 1, wherein switching the frequency improves a visibility of the B-wave oscillations.

4. The system of claim 1, wherein switching the frequency of the ultrasound emitter comprises switching from a first transducer configured for emitting a first ultrasound at a first frequency to a second transducer configured for emitting a second ultrasound at a second frequency.

5. The system of claim 4, wherein all transducers of one or more transducers switch from a first frequency to a second frequency.

6. The system of claim 4, wherein the frequency of the ultrasound energy is switched between about 1.5 to about 3 MHz and about 0.1 to about 1.4 MHz.

7. The system of claim 5, wherein switching from about 1.5 to about 3 MHz to about 0.1 to about 1.4 MHz increases intracranial penetration for B-wave detection in patients with increased skull thickness or calcification.

8. The system of claim 1, wherein the one or more signal quality metrics are a reduction in signal penetration, a reflection, or an amplitude detected at an initial operating frequency of the ultrasound data.

9. The system of claim 4, wherein the one or more signal quality metrics is a detection of a drop below a signal-to-noise ratio (SNR) threshold.

10. The system of claim 4, wherein the switching occurs in real time without manual intervention.

11. The system of claim 4, wherein the ultrasound emitter comprises one or more transducers, wherein the one or more transducers are configured for emitting the first ultrasound, the second ultrasound, or both the first ultrasound and the second ultrasound.

12. The system of claim 11, wherein the one or more transducers comprise capacitive micromachined ultrasonic transducers (CMUTs), piezoelectric microlaminated elements, or a combination thereof.

13. The system of claim 7, wherein frequency switching is reversed from about 1.5 to about 3 MHz to about 0.1 to about 1.4 MHz when the one or more signal quality metrics meet an operational threshold.

14. The system of claim 1, wherein the smart device is further configured to generate a glymphatic index output derived from an amplitude and a frequency of the B-wave oscillations.

15. The system of claim 14, wherein the smart device is further configured to display the glymphatic index output before and after administering neuromodulation or intervention.

* * * * *